United States Patent
Cho

(10) Patent No.: US 11,933,741 B2
(45) Date of Patent: Mar. 19, 2024

(54) METHOD FOR EVALUATION OF RESIN ALLOY

(71) Applicant: LG Chem, Ltd., Seoul (KR)

(72) Inventor: Narae Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 698 days.

(21) Appl. No.: 17/057,409

(22) PCT Filed: Nov. 6, 2019

(86) PCT No.: PCT/KR2019/014987
§ 371 (c)(1),
(2) Date: Nov. 20, 2020

(87) PCT Pub. No.: WO2020/105911
PCT Pub. Date: May 28, 2020

(65) Prior Publication Data
US 2021/0199601 A1    Jul. 1, 2021

(30) Foreign Application Priority Data
Nov. 23, 2018   (KR) .................. 10-2018-0145814

(51) Int. Cl.
*G01N 23/04*    (2018.01)
*G01N 23/06*    (2018.01)
*G01N 33/44*    (2006.01)

(52) U.S. Cl.
CPC ............. *G01N 23/04* (2013.01); *G01N 23/06* (2013.01); *G01N 33/442* (2013.01)

(58) Field of Classification Search
CPC ...... G01N 23/04; G01N 23/06; G01N 33/442; G01N 33/44
See application file for complete search history.

(56) References Cited

U.S. PATENT DOCUMENTS

2017/0320782 A1    11/2017   Tierney et al.

FOREIGN PATENT DOCUMENTS

| EP | 0269748 A1 |   | 6/1988 |
|----|------------|---|--------|
| JP | H07037563 B2 |   | 4/1995 |
| JP | H11125588 A |   | 5/1999 |
| JP | 2004003881 A |   | 1/2004 |
| JP | 3796025 B2 | * | 7/2006 |
| JP | 2011169763 A | * | 9/2011 |
| JP | 2011169763 A |   | 9/2011 |
| JP | 2014190883 A |   | 10/2014 |
| JP | 2017129407 A |   | 7/2017 |
| KR | 20130020477 A |   | 2/2013 |

(Continued)

OTHER PUBLICATIONS

Search report from International Application No. PCT/KR2019/014987, dated Mar. 4, 2020.

(Continued)

*Primary Examiner* — David E Smith
(74) *Attorney, Agent, or Firm* — Lerner David LLP

(57) ABSTRACT

A method for evaluation of a resin alloy includes identifying and quantifying individual materials contained in the resin alloy. In addition, the method can identify encapsulation and whether or not a single phase is formed, without an additional equipment, allowing easier analysis and evaluation of various alloy materials through evaluation of physical properties of resin alloys.

10 Claims, 7 Drawing Sheets

(56) References Cited

FOREIGN PATENT DOCUMENTS

| KR | 20170058702 A | 5/2017 |
|---|---|---|
| WO | 8707285 A1 | 12/1987 |

OTHER PUBLICATIONS

Guo, H. F., et al., "Prediction and manipulation of the phase morphologies of multiphase polymer blends: 1.Ternary systems." Polymer, vol. 38, No. 4, 1997 Elsevier Science Ltd. (revised Apr. 25, 1996'; published Feb. 1997), pp. 785-794.

Wong, S.-C., et al., "Effect of rubber functionality on microstructures and fracture toughness of impact-modified nylon, 6,6/polypropylene blends: 1. Strucutre-property relationships." Polymer, vol. 40, 1999 (revised Apr. 24, 1998, accepted May 7, 1998; published Jun. 2000), pp. 1553-1556.

Wu, Y. et al., "Toughening Effects of "Core-Shell" Particles in PA6/SEBS-g-MA/PPO Blends" Journal of Chemical Engineering of Chinese Universities, Dec. 2017, pp. 1327-1332, vol. 31, No. 6.

Feng, W. et al., "Morphology and impact property of poly( phenylene oxide) I polyamide/(ethylene-1-octene) copolymer blends" Journal of Beijing University of Chemical Technology, Dec. 1999, pp. 30-33 , vol. 26, No. 3.

\* cited by examiner

[Fig. 1]
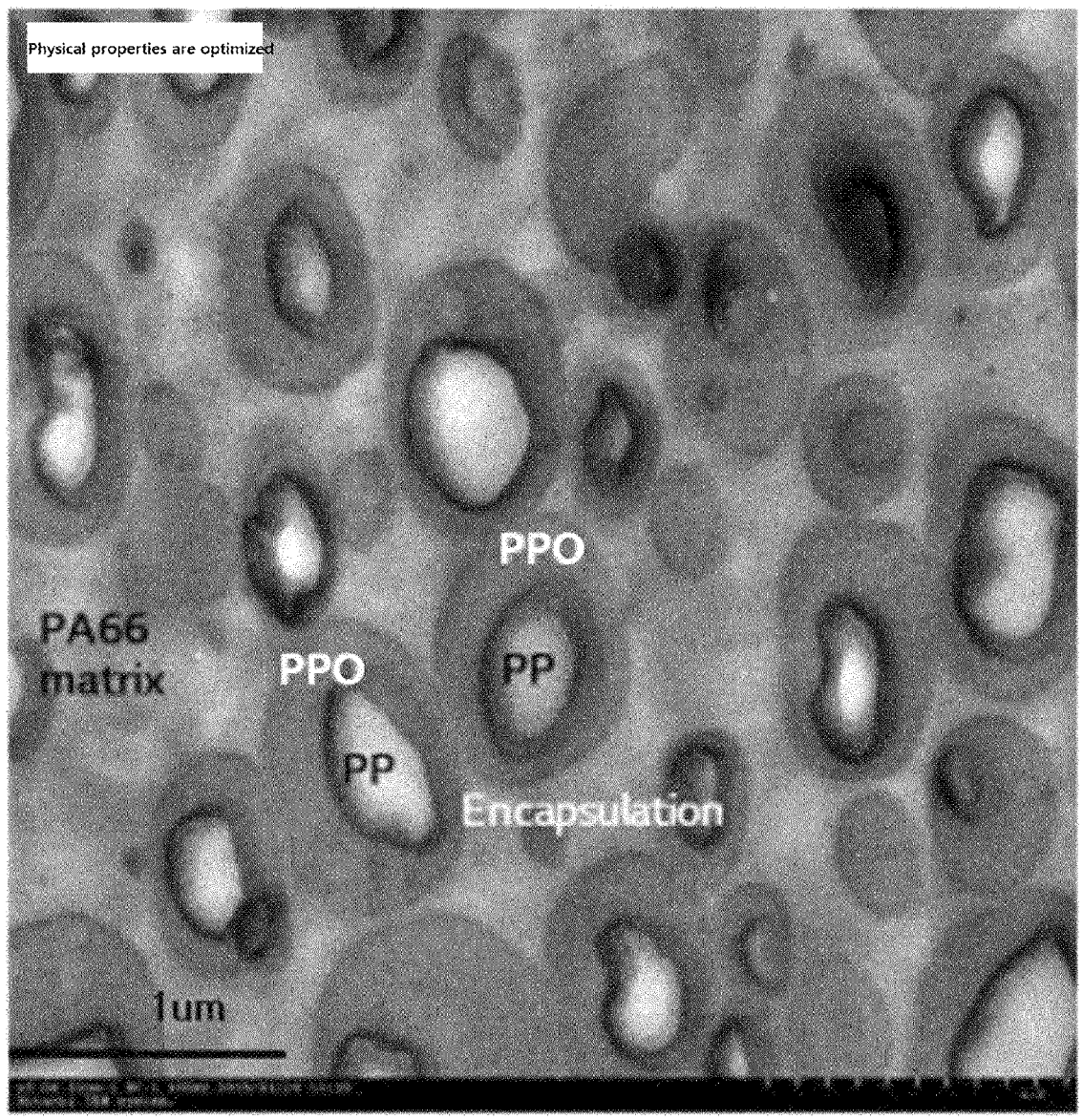

[Fig. 2]
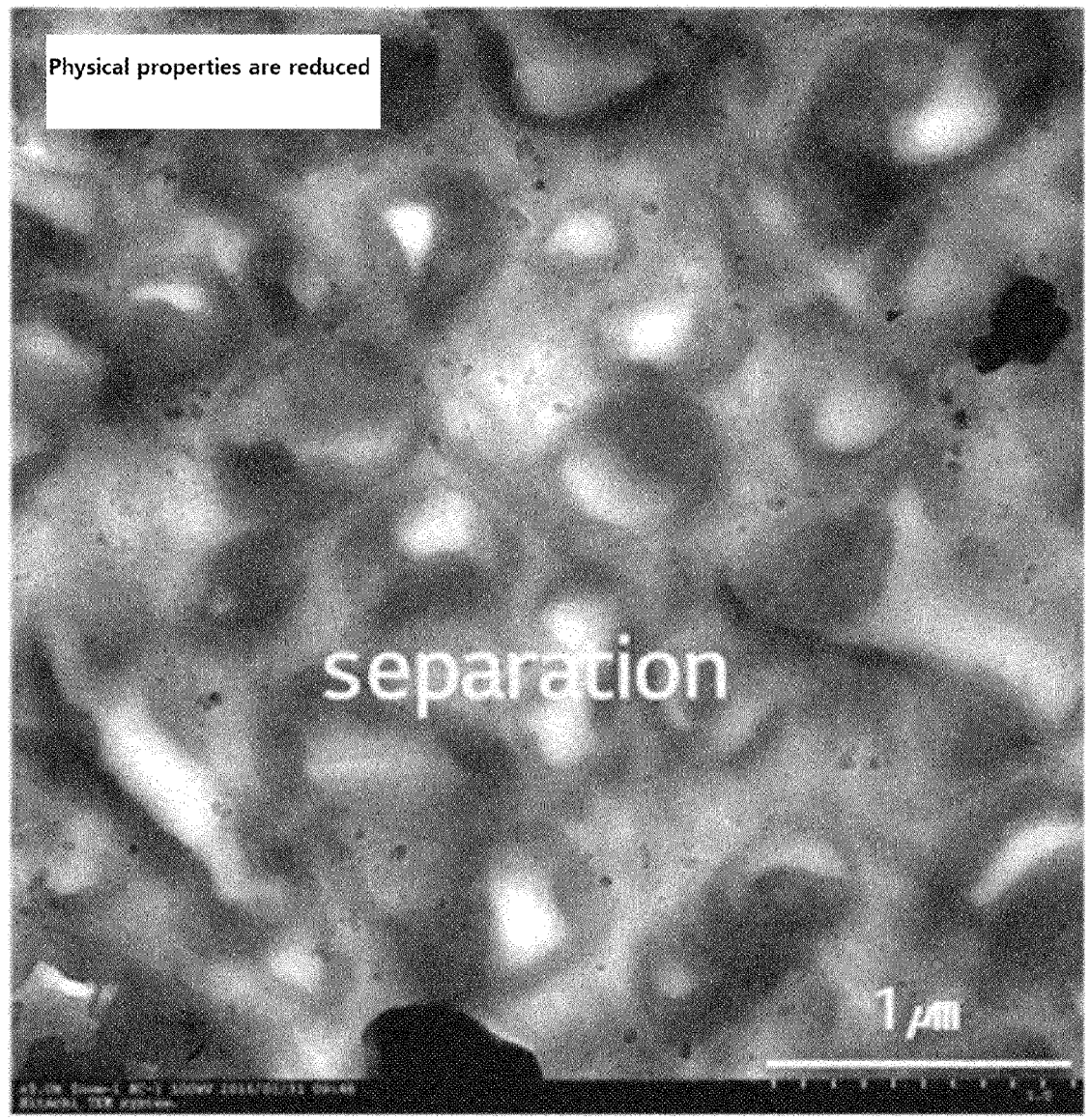

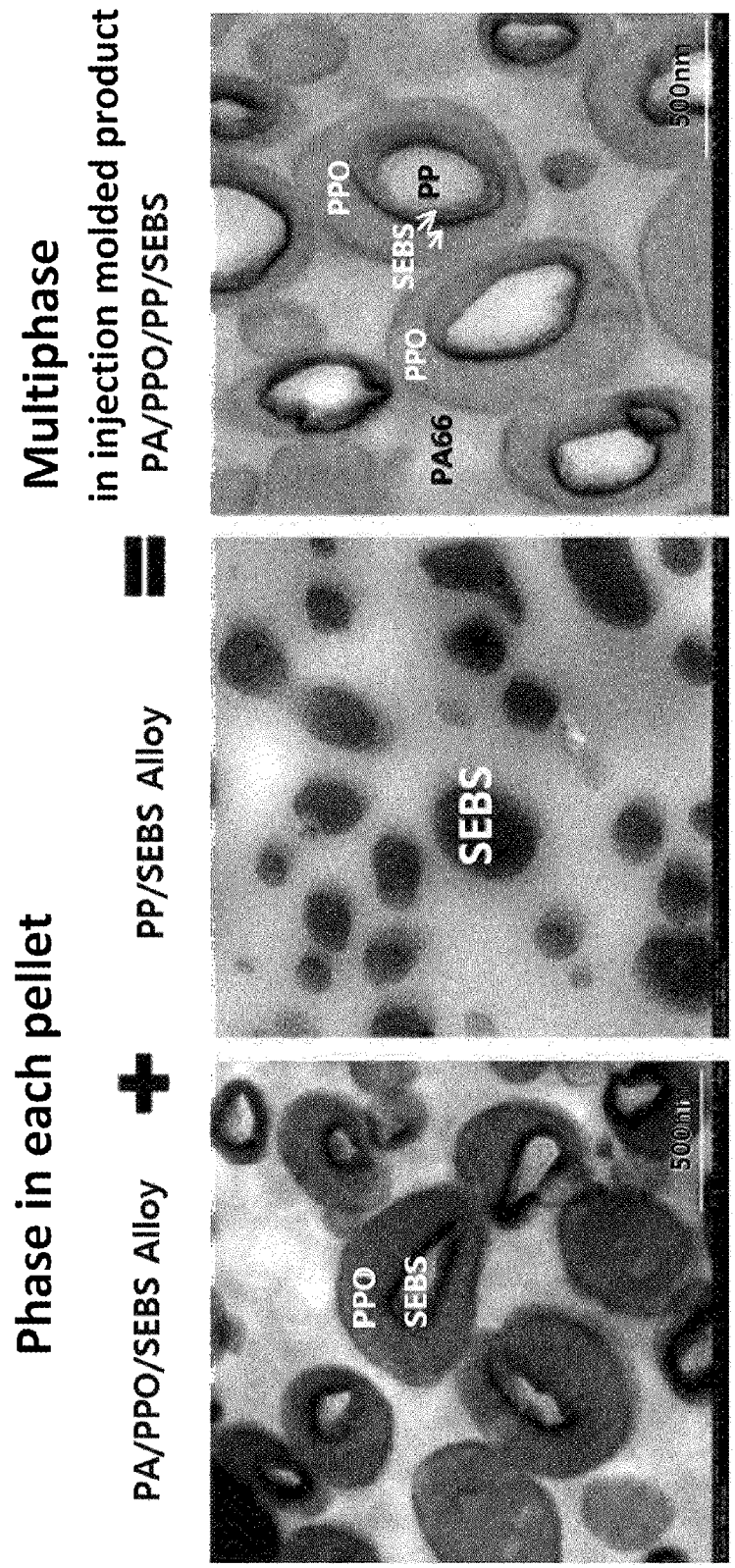
[Fig. 3]

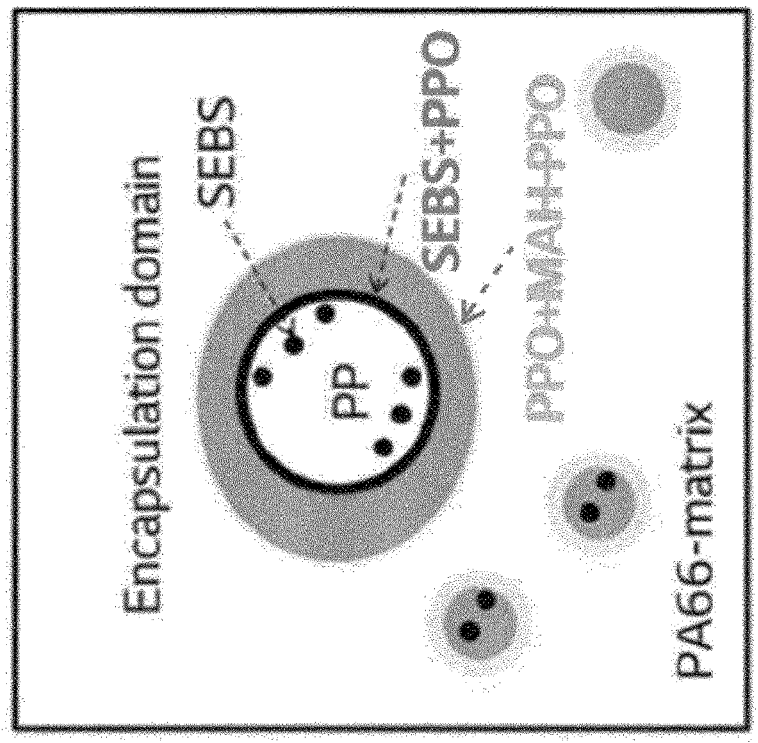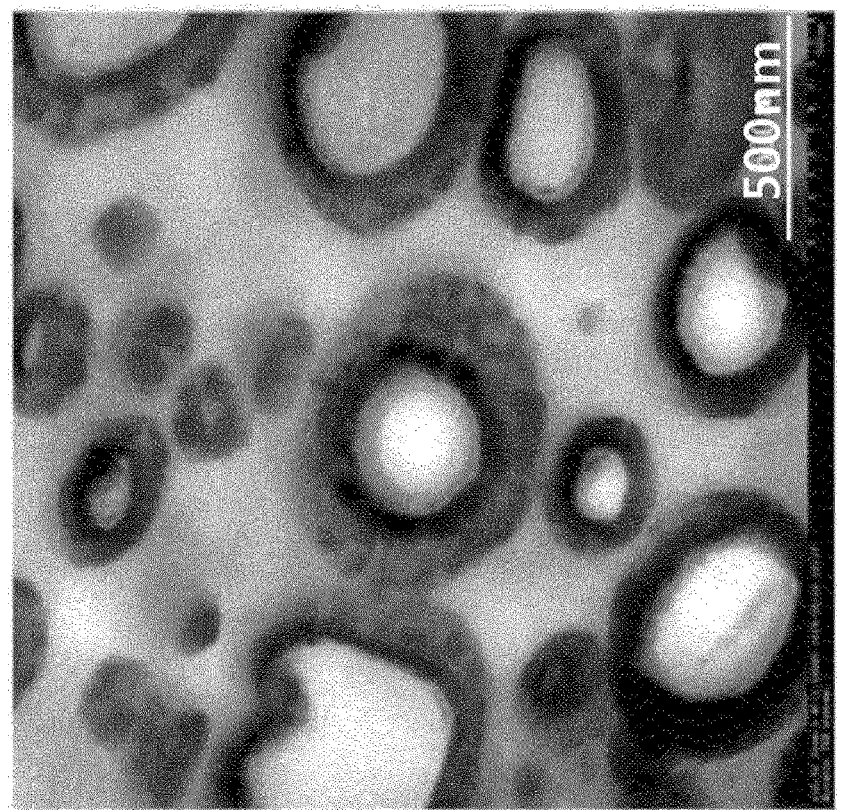
[Fig. 4]

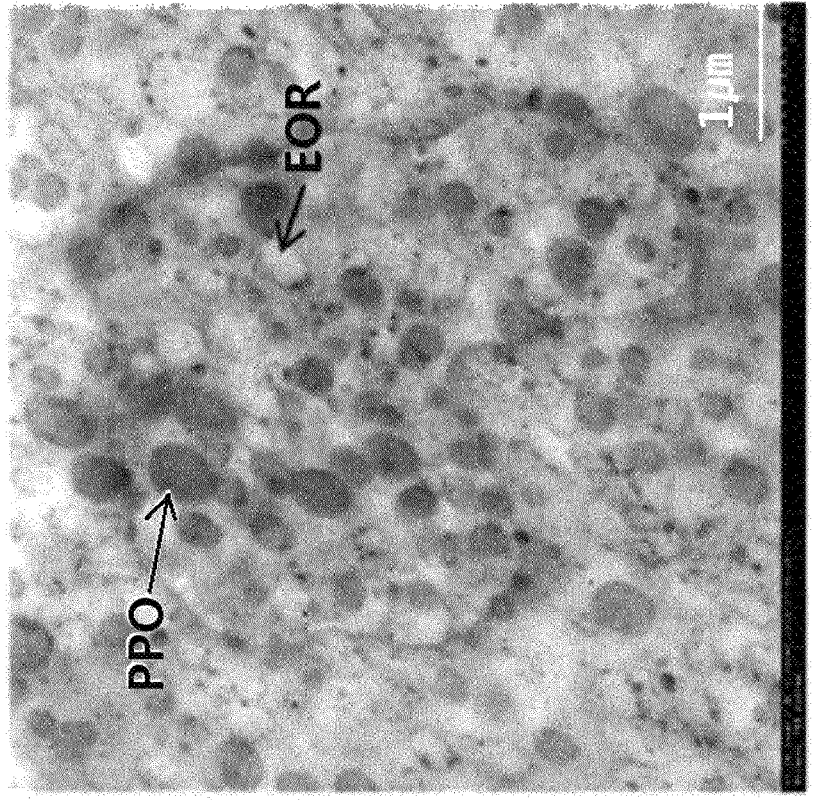
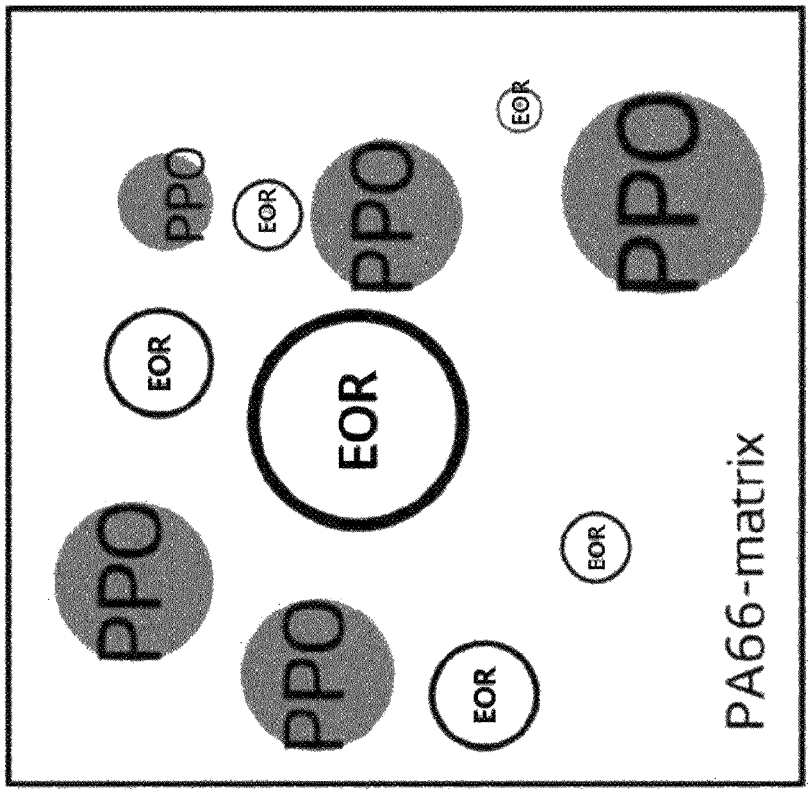
[Fig. 5]

[Fig. 6]
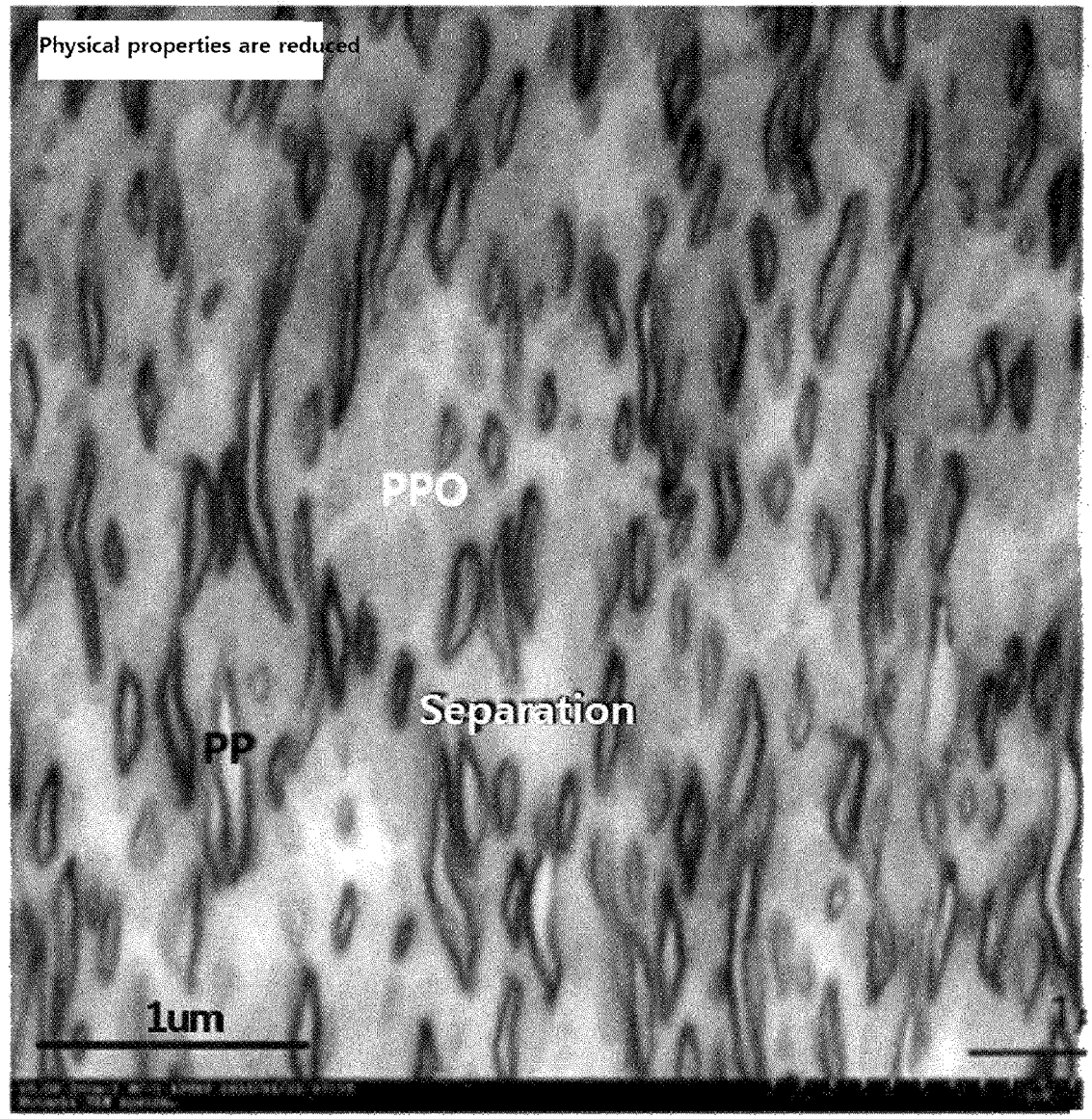

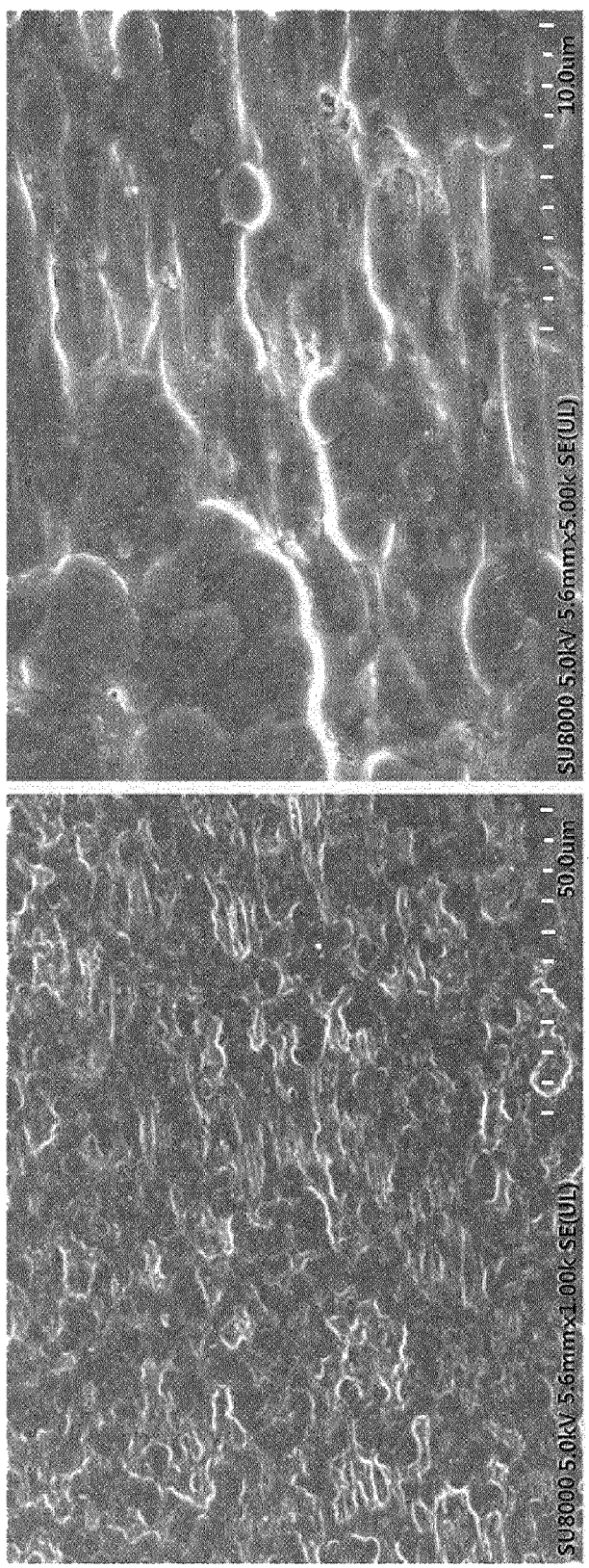
[Fig. 7]

METHOD FOR EVALUATION OF RESIN ALLOY

CROSS-REFERENCE TO RELATED APPLICATIONS

The present application is a national phase entry under 35 U.S.C. § 371 of International Application No. PCT/KR2019/014987 filed Nov. 6, 2019, which claims priority from Korean Application No. 10-2018-0145814 filed Nov. 23, 2018, all of which are incorporated herein by reference.

BACKGROUND OF THE INVENTION

1. Field of the Invention

The present invention relates to a method for observing and evaluating phase behavior of alloy resin.

2. Description of the Related Art

Synthetic resins have various types, which can be selected according to the use. Among them, polyphenylene oxide (PPO) has a characteristic of having very high glass transition temperature (Tg) of 220° C., which is evaluated to be excellent in terms of heat resistance and dimensional stability but has limitations as an injection molding material. On the other hand, nylon (PA) has good fluidity and fire resistance, so that it may have complementary characteristics when forming a base in the form of alloy with PPO.

PA/PPO alloy has been developed to compensate for disadvantages of each of these materials. The addition of rubber to PA/PPO alloy can further improve impact strength at room temperature and low temperature. Materials based on the PA/PPO alloy do not burn at high temperature and do not undergo morphological deformation but have difficulties in developing alloy materials due to the large difference in viscosity between PA and PPO base.

The PA/PPO alloy material is suitable for a fireman's helmet. If it has reinforced dimensional stability, it can be applied to a variety of products such as an automobile wheel cover material.

As such, various composite materials, such as PA-based materials, have been developed and commercialized. However, in order to develop materials having high heat resistance and high impact properties by adding additional materials such as PPO and rubber, it is necessary to understand the relationship between the phase formed by individual material constituting the composite and the physical properties.

Conventionally, in order to analyze resin alloys, fracture appearance of injection molded products was observed by a scanning electron microscope (SEM), or flakes of injection molded products after staining were observed by a transmission electron microscope (TEM).

However, this method has a problem in that it is difficult to distinguish each phase from multi-phase obtained by microscopic observation, because it is difficult to distinguish phases of each material constituting synthetic resin alloys.

Therefore, there is a need for a method for accurately evaluating phase behavior of individual material constituting resin alloy.

SUMMARY OF THE INVENTION

It is an object of the present invention to provide a method for evaluating resin alloy by observing phase behavior of materials constituting the resin alloy.

In order to solve the above problems, the present invention provides a method for evaluating resin alloy, the method comprising the steps of:
- observing phases of each of at least one material constituting the alloy;
- observing multi-phase of the resin alloy; and
- identifying phase behavior for each material from information of the phase of each of at least one material constituting the alloy and of the multi-phase of the resin alloy.

According to one embodiment, a transmission electron microscope (TEM) image may be used in observing the phase or multi-phase.

According to one embodiment, the material may comprise at least one selected from the group consisting of nylon (PA), polyphenylene oxide (PPO), polypropylene (PP), styrene-ethylene-butylene-styrene (SEBS), synthetic rubber and maleic anhydride (MAH).

According to one embodiment, the synthetic rubber may comprise at least one selected from the group consisting of SIS (styrene-isoprene-styrene), SEBS (styrene-ethylene-butylene-styrene), SBS (styrene-butadiene-styrene), EPR (ethylene-propylene rubber), EPDM (ethylene-propylene-diene rubber) and EOR (ethylene-octene rubber).

According to one embodiment, the method may comprise preparing flakes of the individual material and the resin alloy using an ultramicrotome.

In addition, it may comprise staining the flakes with ruthenium tetraoxide ($RuO_4$).

According to one embodiment, the staining may be to vapor staining for 15 to 30 minutes at room temperature.

According to one embodiment, the method may comprise determining whether an encapsulation domain or a single phase is formed for the phase or the multi-phase.

According to one embodiment, the method may comprise quantifying image of the phase or the multi-phase.

According to one embodiment, the physical properties of the resin alloy may be evaluated from the information of the phase behavior.

Other specific details of embodiments of the present invention are included in the following detailed description.

Effect of the Invention

According to the present invention, it is possible to distinguish and quantify individual material contained in the resin alloy. In addition, since the physical properties of the resin alloy can be evaluated by confirming encapsulation and formation of a single phase without additional equipment, it is possible to readily apply to the analysis and evaluation of various alloy materials.

BRIEF DESCRIPTION OF THE DRAWINGS

FIG. 1 is a transmission electron microscope (TEM) observation image according to Example 1.

FIG. 2 is a transmission electron microscope (TEM) observation image according to Example 2.

FIG. 3 is a transmission electron microscope (TEM) observation image according to Examples 3 to 5.

FIG. 4 shows observation of encapsulation domain.

FIG. 5 shows observation of formation state of a single phase.

FIG. 6 is a transmission electron microscope (TEM) observation image according to Example 8.

FIG. 7 is a scanning electron microscope (SEM) observation image according to Comparative Example 1.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

The term "addition" as used herein may be described interchangeably with "feeding", "inflow", "injection", and may be understood to mean flowing or putting solid, liquid, gas or heat, etc. into the places in a need thereof.

Hereinafter, the method for evaluating resin alloy according to the embodiment of the present invention will be described in more detail.

The present invention relates to a method for evaluating resin alloy, the method comprising the steps of:
- observing phases of each of at least one material constituting the alloy;
- observing multi-phase of the resin alloy; and
- identifying phase behavior for individual material from information of the phase of each of at least one material constituting the alloy and of the multi-phase of the resin alloy.

According to one embodiment, a transmission electron microscope (TEM) image may be used in observing the phase of at least one material constituting the alloy or of the multi-phase of the resin alloy. A scanning electron microscope (SEM) is easy to observe the surface or three-dimensional structure of the sample and a transmission electron microscope is easy to observe the cross section of the sample. Therefore, a transmission electron microscope can be used to observe flakes of the sample.

According to one embodiment, the resin alloy that can be analyzed according to the present invention may be composed of two or more materials, for example it may include at least one selected from the group consisting of nylon (PA), polyphenylene oxide (PPO), polypropylene (PP), styrene-ethylene-butylene-styrene (SEBS), rubber and maleic anhydride (MAH).

Materials such as PA and PPO have advantages in terms of properties such as heat resistance and fluidity. However, their molding properties and impact strength are not sufficient to implement a product, and therefore a material such as rubber can be added to reinforce insufficient properties. Examples of the rubber include, for example, at least one selected from the group consisting of SIS (styrene-isoprene-styrene), SEBS (styrene-ethylene-butylene-styrene), SBS (styrene-butadiene-styrene), EPR (ethylene-propylene rubber), EPDM (ethylene-propylene-diene rubber) and EOR (ethylene-octene rubber). The rubber may be used without particular limitation as long as it is a rubber generally included in synthetic resins, and various types of rubber may allow distinguishing each phase after dyeing with a staining agent.

The materials to be included in the resin alloy is not particularly limited as long as it is a material generally included in synthetic resins in addition to those described above.

According to one embodiment, an ultramicrotome may be used in order to observe the resin alloy and one or more materials constituting the alloy with an electron microscope. Specifically, for example, flakes can be formed at a low temperature of $-120°$ C. Each sample flake formed can be evaluated by observing under a microscope after the staining process.

From the observation results, it is possible to determine whether an encapsulation domain or a single phase is formed and to perform quantitative analysis through image quantification. In addition, it is possible to improve the properties of the material to meet the purpose of the product, by understanding the relationship between the physical properties and the phase behavior.

Hereinafter, embodiments of the present invention will be described in detail so that those skilled in the art can easily carry out the present invention. The present invention may, however, be embodied in many different forms and should not be construed as limited to the embodiments set forth herein.

Example 1

45% nylon 66 (PA66), 35% polyphenylene oxide (PPO), 10% polypropylene (PP), 4% styrene-ethylene-butylene-styrene (SEBS), 5% PPE-MAH and 1% additive were mixed by a mixer and fed to a main feeder of a twin screw extruder (L/D=45, $\phi$=40). Thereafter, a resin composition in pellet form was prepared by melting, kneading and extruding at a temperature of 270 to 290° C. and 250 to 350 rpm. Subsequently, flakes were prepared at $-120°$ C. using an ultramicrotome (Leica EM UC7).

The resulting resin composition chips in pellet form were dried at 110° C. for 6 hours to prepare an injection molded product using a screw injection machine heated to 260 to 300° C. and a mold temperature of 80 to 130° C. For the injection molded product, flakes were prepared in the same manner as above.

Each flake was vapor stained at room temperature with ruthenium tetraoxide ($RuO_4$) in an aqueous solution for 15 to 30 minutes, and then observed by a transmission electron microscope (TEM, Hitachi H-7650). TEM image is shown in FIG. 1.

As shown in FIG. 1, it is observed that each of the phases has a distinct encapsulation shape. The optimization of physical properties can be explained by the encapsulation.

Example 2

Flakes were prepared and evaluated in the same manner as in Example 1, except that an injection molded product having a composition of 45% nylon 66 (PA66), 35% polyphenylene oxide (PPO), 10% PP, 4% styrene-ethylene-butylene-styrene (SEBS), 5% PPE-MAH and 1% additive and a specific gravity of 1.06 and an impact strength of 10 was used. The results are shown in FIG. 2 and it is found that physical properties of the resin alloy are reduced as shown in FIG. 2.

Examples 3 to 5

It was evaluated in the same manner as in Example 1, except that the composition was as follows, and the results are shown in FIG. 3.

Example 3: PA/PPO/SEBS alloy (left photo of FIG. 3), PA66 55%, PPO 34%, SEBS 6%, compatibilizer 5%, Example 4: PP/SEBS/alloy (middle photo of FIG. 3), PP 80% SEBS 20% (PP is used as matrix)

Example 5: PA/PPO/PP/SEBS alloy (right photo of FIG. 3), PA66 45%, PPO 34%, PP 10%, compatibilizer 5%, SEBS 6%

As a result of examining the phase for individual material of the resin alloy composed of two or more materials, as shown in FIG. 3, the photo on the right shows the multi-phase of the injection molded product. It is found that four or more phases exist separately. In particular, by identification of the behavior of the styrene-ethylene-butylene-styrene (SEBS) from staining results of the nylon (PA) matrix (left photo of FIG. 3) and the polypropylene (PP) matrix (middle photo of FIG. 3), it can be seen that SEBS behaves in the interior of encapsulated polypropylene (PP) and polyphenylene ether (PPE).

Example 6

Resin alloy was evaluated in the same manner as in Example 1, except for having a composition of 64% PA66, 30% PPO, 8% PP, 10% compatibilizer, 6% SEBS and the results are shown in FIG. 4. As shown in FIG. 4, aromatic rings of the phase in the alloy are stained with $RuO_4$ to obtain a dark contrast TEM image. The affinity of each phase is analyzed to be SEBS>SEBS+PPO>PPO+MAH-PPO>PA66 (PA66 is not stained and thus observed as a white region of the brightest contrast), thereby distinguishing each phase. Through this, the encapsulation domain in the PA alloy can be observed.

Example 7

Resin alloy was evaluated in the same manner as in Example 1, except for having a composition of 60% PA66, 15% PPO, 5% compatibilizer and 20% EOR and the results are shown in FIG. 5. It is possible to distinguish and analyze each phase of various alloys using the affinity of each phase after staining the aromatic rings in each phase with a $RuO_4$ staining agent. The affinity of each phase is PPO>EOR>PA66, and PA66 is not stained and thus observed as a white region of the brightest contrast.

Example 8

Resin alloy was evaluated in the same manner as in Example 1, except for having a composition of 45% PA, 40% PPE-MAH, 10% PP, 4% SEBS and 1% additive and the results are shown in FIG. 6. The affinity of each phase is SEBS>PPO>PA and it is found that each phase was separated, not an encapsulation form. In Examples 5 to 8, it is possible to distinguish and analyze each phase of various alloys using the affinity of each phase after staining the aromatic rings in each phase with a $RuO_4$ staining agent.

Comparative Example 1

SEM cross section was prepared at −120° C. using an ultramicrotome (Leica EM UC7) for the same injection molded product as used in Example 1. The SEM cross section was observed with a scanning electron microscope (SEM, Hitachi SU8020) without staining. The SEM image is shown in FIG. 7. As shown in FIG. 7, it is found that SEM observation without pretreatment such as staining or etching has difficulty in distinguishing each phase.

Experimental Example 1: Relationship Between Phase Behavior and Physical Properties In order to confirm the relationship between the phase behavior and the physical properties of the resin alloy, first, physical properties of the injection molded products according to Examples 1 and 2 were measured.

Specific gravity was measured using a specific gravity meter according to ASTM D792 standard, and impact strength (Notched Izod, kgf·cm/cm$^2$) was measured using a ¼" specimen according to ASTM D256 standard. The results are shown in Table 1.

In addition, weather resistance for Example 1 was evaluated according to the ASTG155 standard, and the occurrence of whitening was checked, and the result value was 20.

TABLE 1

| Item | Example 1 | Example 2 |
| --- | --- | --- |
| Specific viscosity | 1.06 | 1.06 |
| Impact strength | 20 | 10 |

As shown in Table 1, it was confirmed by the numerical result values that the physical properties of Example 1 of FIG. 1 are optimized compared to the physical properties of Example 2 of FIG. 2.

According to the method of the present invention as described above, it is possible to improve the problem that it is difficult to recognize the phase for individual material constituting the resin alloy in the case of staining the injection molded product of the resin alloy at once by the conventional method, thereby acquiring a clear phase behavior image.

Quantitative data can be obtained through quantification of the acquired image, and the quantitative data can be used as data for improving the characteristics of the composition by analyzing the relationship with physical properties.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A method for evaluating resin alloy, the method comprising:
   preparing flakes of the resin alloy and of an individual material of the resin alloy,
   staining the flakes,
   observing a phase of each of at least one material constituting the resin alloy to form an information of the phase of each of the at least one material constituting the resin alloy;
   observing a multi-phase of the resin alloy to form an information of the multi-phase of the resin; and
   identifying a phase behavior for the individual material of the resin alloy from the information of the phase of each of the at least one material constituting the resin alloy and of the information of the multi-phase of the resin alloy.

2. The method for evaluating resin alloy according to claim 1, wherein a transmission electron microscope (TEM) image is used in the observing the phase or the observing the multi-phase.

3. The method for evaluating resin alloy according to claim 1, wherein the at least one material comprises at least one selected from the group consisting of nylon (PA), polyphenylene oxide (PPO), polypropylene (PP), styrene-ethylene-butylene-styrene (SEBS), synthetic rubber and maleic anhydride (MAH).

4. The method for evaluating resin alloy according to claim 3, wherein the synthetic rubber comprises at least one selected from the group consisting of SIS (styrene-isoprene-styrene), SEBS (styrene-ethylene-butylene-styrene), SBS (styrene-butadiene-styrene), EPR (ethylene-propylene rubber), EPDM (ethylene-propylene-diene rubber) and EOR (ethylene-octene rubber).

5. The method for evaluating resin alloy according to claim 1, wherein the preparing uses an ultramicrotome.

6. The method for evaluating resin alloy according to claim 5, wherein the staining includes ruthenium tetraoxide ($RuO_4$).

7. The method for evaluating resin alloy according to claim 6, wherein the staining comprises vapor staining for 15 to 30 minutes at room temperature.

8. The method for evaluating resin alloy according to claim 1, further comprising determining whether an encapsulation domain or a single phase is formed for the phase or the multi-phase.

9. The method for evaluating resin alloy according to claim 1, further comprising quantifying image of the phase or the multi-phase.

10. The method for evaluating resin alloy according to claim 1, wherein physical properties of the resin alloy are evaluated from information of the phase behavior.

\* \* \* \* \*